(12) United States Patent
Dextradeur et al.

(10) Patent No.: US 9,220,877 B2
(45) Date of Patent: Dec. 29, 2015

(54) MULTI-BRANCHED ANTI-REFLUX VALVE

(75) Inventors: Alan J. Dextradeur, Franklin, MA (US); Robert Kraus, Attleboro, MA (US)

(73) Assignee: DEPUY SYNTHES PRODUCTS, INC., Raynham ( * ) Notice: Subject to any disclaimer, the term of this patent is extended or adjusted under 35 U.S.C. 154(b) by 951 days.

(21) Appl. No.: 12/772,847

(22) Filed: May 3, 2010

(65) Prior Publication Data

US 2010/0210992 A1    Aug. 19, 2010

Related U.S. Application Data

(62) Division of application No. 11/212,412, filed on Aug. 27, 2005, now abandoned.

(51) Int. Cl.
*A61M 31/00* (2006.01)
*A61M 27/00* (2006.01)

(52) U.S. Cl.
CPC .................... *A61M 27/006* (2013.01)

(58) Field of Classification Search
CPC ............... A61M 2025/004; A61M 2025/0681; A61M 2210/0693
USPC ............. 604/500–504, 8–10, 247, 512.1, 539
See application file for complete search history.

(56) References Cited

U.S. PATENT DOCUMENTS

| | | | |
|---|---|---|---|
| 2,866,457 A | 12/1958 | Moore | |
| 4,072,153 A | 2/1978 | Swartz | |
| 4,432,853 A | 2/1984 | Banks | |
| 4,595,390 A | 6/1986 | Hakim | |
| 4,615,691 A | 10/1986 | Hakim | |
| 4,681,559 A * | 7/1987 | Hooven | 604/9 |
| 4,712,551 A | 12/1987 | Rayhanabad | |
| 4,772,257 A | 9/1988 | Hakim | |
| 4,979,937 A | 12/1990 | Khorasani | |
| 5,575,767 A | 11/1996 | Stevens | |
| 5,755,773 A | 5/1998 | Evans | |
| 5,906,641 A | 5/1999 | Thompson | |
| 5,928,182 A | 7/1999 | Kraus | |
| 6,086,553 A | 7/2000 | Akbik | |
| 6,554,790 B1 | 4/2003 | Moll | |
| 6,689,085 B1 | 2/2004 | Rubenstein | |
| 6,817,985 B2 | 11/2004 | Barbut | |
| 6,859,953 B1 | 3/2005 | Christensen | |
| 6,866,647 B2 | 3/2005 | Barbut | |
| 2003/0135148 A1 * | 7/2003 | Dextradeur et al. | 604/8 |

* cited by examiner

*Primary Examiner* — Phillip Gray

(57) ABSTRACT

A shunt system includes a first catheter and a second catheter, each having a proximal end and a distal end, and at least one opening adjacent to its distal end. A proximal end of a drainage catheter is in fluid communication with the proximal end of the first catheter and the proximal end of the second catheter. A first one-way valve is disposed in fluid communication with the first catheter between its proximal end and its at least one opening. The first one-way valve effectively blocks fluid flow from the proximal end to the at least one opening. A second one-way valve is disposed in fluid communication with the second catheter between its proximal end and its at least one opening. The second one-way valve effectively blocks fluid flow from the proximal end to the at least one opening.

3 Claims, 3 Drawing Sheets

MULTI-BRANCHED ANTI-REFLUX VALVE

CROSS-REFERENCE TO RELATED APPLICATIONS

The present application is a divisional of U.S. patent application Ser. No. 11/212,412 filed Aug. 27, 2005.

STATEMENT REGARDING FEDERALLY SPONSORED RESEARCH

Not Applicable.

FIELD OF THE INVENTION

The present invention relates to a multi-branched anti-reflux valve. More specifically, the present invention relates to a system and method for draining fluid from multiple drainage sites within the human brain.

BACKGROUND OF THE INVENTION

Hydrocephalus is most often treated by surgically inserting a shunt. The shunt diverts the flow of cerebrospinal fluid ("CSF") from the ventricles of the brain to another area of the body where the CSF can be absorbed as part of the circulatory system. A shunt typically includes a ventricular catheter that is introduced through a burr hole in the skull and implanted in the patient's ventricle. A drainage catheter delivers the CSF to its ultimate drainage site (e.g., the peritoneum). Optionally, a valve may be used to regulate the one-way flow of CSF from the patient's ventricle to the drainage site.

To drain fluid from more than one site, a surgeon has used multiple shunts. That is, a first shunt, having its own ventricular catheter and drainage catheter, is used to drain CSF from a first site, and a second shunt, having its own ventricular catheter and drainage catheter, is used to drain CSF from a second site.

Occasionally the surgeon may have the need to drain fluid from multiple sites within the brain. If the surgeon were to modify the valve construct to drain from multiple sites with a simple Y-connector, cross draining may occur between the two sites within the brain as the CSF will travel along the path of least resistance. Thus, there is the need to provide surgeons with a device that will permit fluid to drain from multiple sites without cross draining occurring.

SUMMARY OF THE INVENTION

The present invention provides these and other needs with a shunt system that includes a first catheter having a proximal end and a distal end. The first catheter has at least one opening adjacent to its distal end. A second catheter has a proximal end and a distal end. The second catheter has at least one opening adjacent to its distal end. A drainage catheter has a proximal end and a distal end. The proximal end of the drainage catheter is in fluid communication with the proximal end of the first catheter and the proximal end of the second catheter. A first one-way valve is disposed in fluid communication with the first catheter between its proximal end and its at least one opening. The first one-way valve permits fluid flow from the at least one opening to the proximal end with approximately zero opening pressure. The first one-way valve effectively blocks fluid flow from the proximal end to the at least one opening. A second one-way valve is disposed in fluid communication with the second catheter between its proximal end and its at least one opening. The second one-way valve permits fluid flow from the at least one opening to the proximal end with approximately zero opening pressure. The second one-way valve effectively blocks fluid flow from the proximal end to the at least one opening. Depending upon the needs of the surgeon however, the two one-way valves could both open with approximately zero opening pressure, or the two one-way valves could both open with a predetermined opening pressure that is greater than zero.

BRIEF DESCRIPTION OF THE DRAWINGS

The invention can be more fully understood from the following detailed description taken in conjunction with the accompanying drawings, in which.

DETAILED DESCRIPTION OF THE INVENTION

Figure 1A:
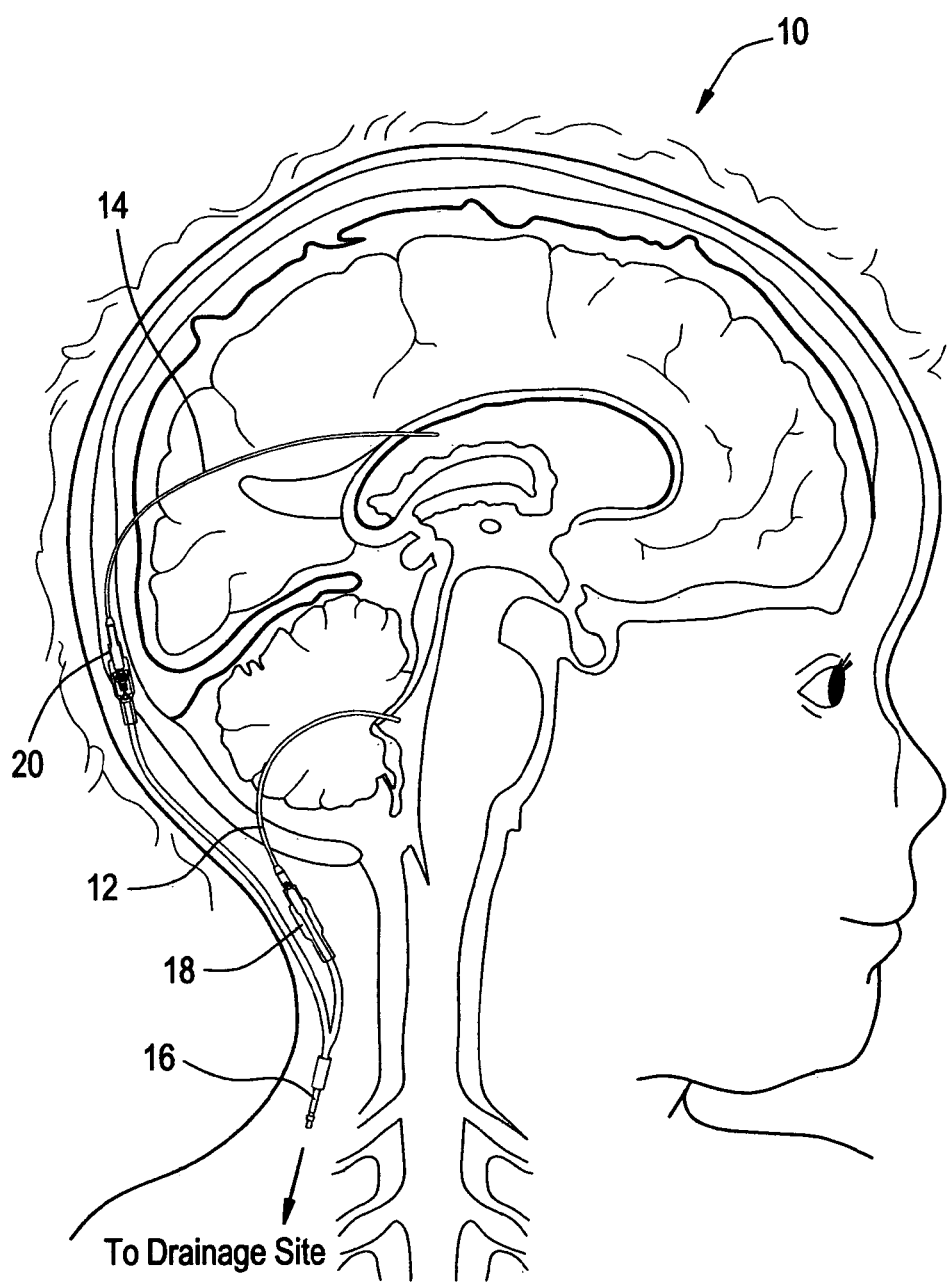
FIG. 1A is a partial sectional view showing a first catheter draining fluid from the lateral ventricle of the human brain, and a second catheter draining fluid from the fourth ventricle of a human brain.

Referring now to FIGS. 1A-2C, a shunt system 10 in accordance with the present invention is illustrated. Referring now to FIG. 1A, a first catheter 12 having a proximal end and a distal end. The first catheter has at least one opening adjacent to its distal end, as is known in the art. A second catheter 14 has a proximal end and a distal end. The second catheter also has at least one opening adjacent to its distal end. A drainage catheter 16 has a proximal end and a distal end. The proximal end of the drainage catheter 16 is in fluid communication with the proximal end of the first catheter and the proximal end of the second catheter. A first one-way valve 18 is disposed in fluid communication with the first catheter 12 between its proximal end and its at least one opening. The first one-way valve permits fluid flow within the first catheter 12 from the at least one opening to the proximal end with approximately zero opening pressure. The first one-way valve also effectively blocks fluid flow within the first catheter 12 from the proximal end to the at least one opening.

A second one-way valve 20 is disposed in fluid communication with the second catheter 14 between the proximal end and the at least one opening. The second one-way valve 20 permits fluid flow within the second catheter 14 from the at least one opening to the proximal end with a predetermined opening pressure that is greater than zero. The second one-way valve also effectively blocks fluid flow within the second catheter 14 from the proximal end to the at least one opening. The first one-way valve 18 and the second one-way valve 20 can be, for example, ball and cone valves or diaphragm valves. The second one-way valve 20 is preferably an adjustable valve so that the threshold or opening pressure that allows fluid flow through a shunt system may vary. U.S. Pat. Nos. 4,595,390, 4,615,691, 4,772,257, and 5,928,182 are exemplary typed of adjustable shunt valves, and the disclosures of which are all hereby incorporated by reference in their entirety. The predetermined opening pressure of the second one-way valve 20 can be adjusted non-invasively with means such as a wireless communications (e.g., magnetically) or a wireless telemetric communication, which includes the transfer of data or other information. The predetermined opening pressure of the second one-way valve 20 is preferably programmable in the range from approximately 10 mmH₂O to approximately 400 mmH₂O, and more preferably from approximately 10 mmH₂O to approximately 200 mmH₂O.

Figure 2A:
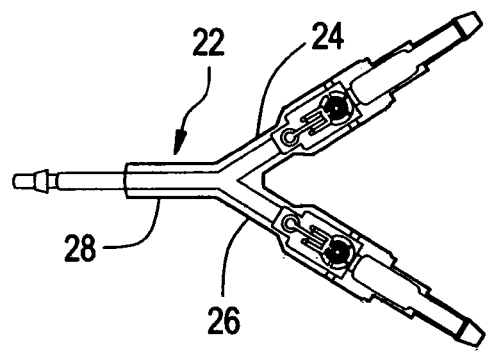
FIG. 2A shows a plan view of a branched drainage conduit, with each conduit having a one-way valve that opens with a predetermined opening pressure that is greater than zero.
Figure 2B:
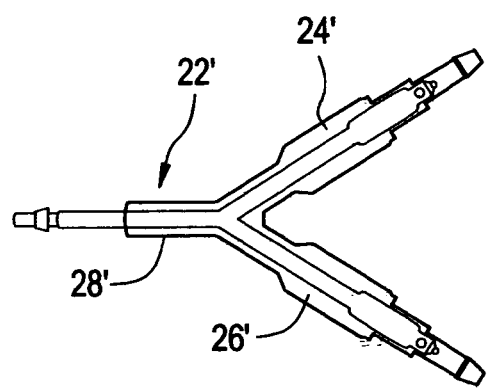
FIG. 2B shows a plan view of a branched drainage conduit, with each conduit having a one-way valve that opens with approximately zero opening pressure.
Figure 2C:
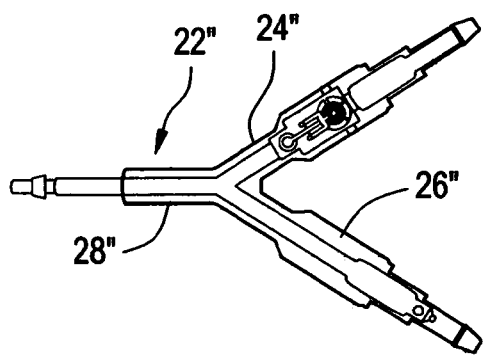
FIG. 2C shows a plan view of a branched drainage conduit, with one conduit having a one-way valve that opens with a predetermined opening pressure that is greater than zero and the other conduit having a one-way valve that opens with approximately zero opening pressure.

Referring now to FIGS. 2A-2C, a connector 22, 22', 22" that may be used to facilitate fluid handling is illustrated. Connector 22, 22', 22" has a first port 24, 24', 24", a second port 26, 26', 26" and a third port 28, 28', 28". The first port is in fluid communication with the proximal end of the first catheter. The second port is in fluid communication with the proximal end of the second catheter, and the third port is in fluid communication with the proximal end of the drainage catheter. The distal end of the drainage catheter is typically placed in the peritoneum. But the fluid could be drained elsewhere in the body, or the system could be used to drain fluid externally from the body.

To use the shunt system 10 to drain cerebral spinal fluid (CSF) from multiple sites within the brain the surgeon will place the proximal end of the drainage catheter in fluid communication with the proximal end of the first catheter and the proximal end of the second catheter. A first one-way valve is placed in fluid communication with the first catheter between its proximal end and the at least one opening such that the first one-way valve permits fluid flow from the at least one opening to the proximal end with a predetermined opening pressure that is greater than zero. The first one-way valve effectively blocks fluid flow from the proximal end to the at least one opening. A second one-way valve is placed in fluid communication with the second catheter between the proximal end and the at least one opening such that the second one-way valve permits fluid flow from the at least one opening to the proximal end with approximately zero opening pressure. The second one-way valve effectively blocks fluid flow from the proximal end to the at least one opening.

Figure 1B:
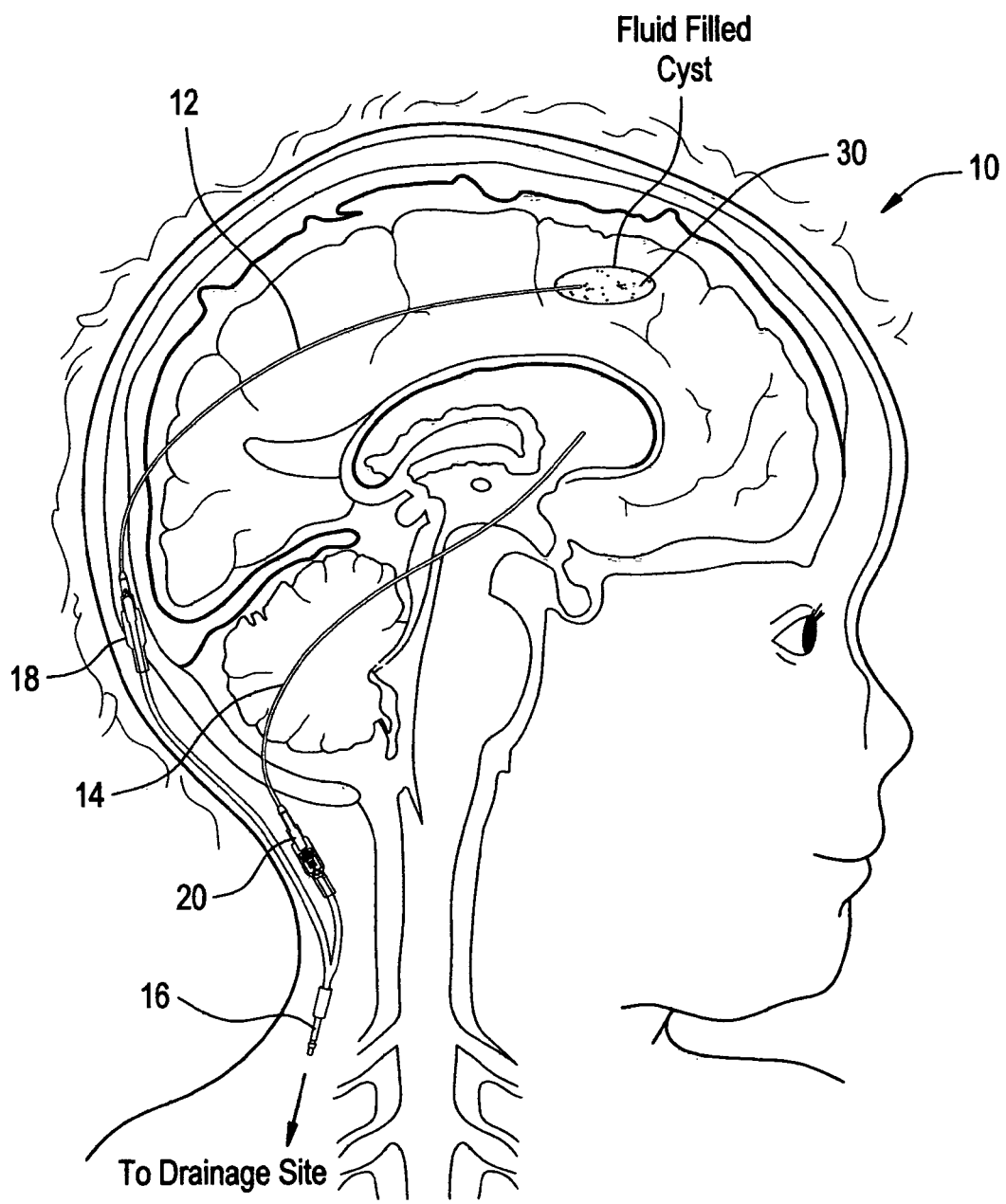
FIG. 1B is a partial sectional view showing a first catheter draining fluid from a fluid filled cyst, and a second catheter draining fluid from the lateral ventricle.

As illustrated in FIG. 1A, the distal end of the first catheter can be placed, for example, in the lateral ventricle, and the distal end of the second catheter can be placed in the fourth ventricle. Alternatively, as illustrated in FIG. 1B, the distal end of the first catheter can be placed, for example, in fluid communication with a fluid filled cyst 30, and the distal end of the second catheter can be placed in the fourth ventricle.

Of course, however, depending upon the needs of the surgeon, the two one-way valves could both open with approximately zero opening pressure as shown in FIG. 2B. Likewise, the two one-way valves could both open with a predetermined opening pressure that is greater than zero as shown in FIG. 2A.

It will be understood that the foregoing is only illustrative of the principles of the invention, and that various modifications can be made by those skilled in the art without departing from the scope and spirit of the invention. All references cited herein are expressly incorporated by reference in their entirety.

One skilled in the art will appreciate further features and advantages of the invention based on the above-described embodiments. While there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps, which perform substantially the same function, in substantially the same way, to achieve the same results are within the scope of the invention. Substitutions of elements from one described embodiment to another are also fully intended and contemplated. It is also to be understood that the drawings are not necessarily drawn to scale, but that they are merely conceptual in nature. Accordingly, the invention is not to be limited by what has been particularly shown and described, except as indicated by the appended claims. All publications and references cited herein are expressly incorporated herein by reference in their entirety.

What is claimed is:

1. A method of draining cerebral spinal fluid (CSF) from multiple sites within the brain with a first catheter having a proximal end and a distal end, said first catheter having at least one opening adjacent to said distal end; a second catheter having a proximal end and a distal end, said second catheter having at least one opening adjacent to said distal end; and a drainage catheter having a proximal end and a distal end; said method comprising the steps of:

placing said proximal end of said drainage catheter in fluid communication with said proximal end of said first catheter and said proximal end of said second catheter;

placing a first one-way valve in fluid communication with said first catheter between said proximal end and said at least one opening such that said first one-way valve permits fluid flow from said at least one opening to said proximal end with approximately zero opening pressure, and said first one-way valve effectively blocks fluid flow from said proximal end to said at least one opening;

placing a distal end of the first catheter in the brain spaced from the ventricles;

placing a second one-way valve in fluid communication with said second catheter between said proximal end and said at least one opening such that said second one-way valve permits fluid flow from said at least one opening to said proximal end with approximately zero opening pressure, said second one-way valve effectively blocks fluid flow from said proximal end to said at least one opening; and placing a distal end of the second catheter in one of the ventricles of the brain.

2. A method of draining cerebral spinal fluid (CSF) from multiple sites within the brain with a first catheter having a proximal end and a distal end, said first catheter having at least one opening adjacent to said distal end; a second catheter having a proximal end and a distal end, said second catheter having at least one opening adjacent to said distal end; and a drainage catheter having a proximal end and a distal end; said method comprising the steps of:

placing said proximal end of said drainage catheter in fluid communication with said proximal end of said first catheter and said proximal end of said second catheter;

placing a first one-way valve in fluid communication with said first catheter between said proximal end and said at least one opening such that said first one-way valve permits fluid flow from said at least one opening to said proximal end with approximately zero opening pressure, and said first one-way valve effectively blocks fluid flow from said proximal end to said at least one opening;

placing a distal end of the first catheter in the brain spaced from the ventricles;

placing a second one-way valve in fluid communication with said second catheter between said proximal end and said at least one opening such that said second one-way valve permits fluid flow from said at least one opening to said proximal end with a predetermined opening pressure greater than zero, said second one-way valve effectively blocks fluid flow from said proximal end to said at least one opening; and placing a distal end of the second catheter in one of the ventricles of the brain.

3. A method of draining cerebral spinal fluid (CSF) from multiple sites within the brain with a first catheter having a proximal end and a distal end, said first catheter having at least one opening adjacent to said distal end; a second catheter having a proximal end and a distal end, said second catheter having at least one opening adjacent to said distal end; and a drainage catheter having a proximal end and a distal end; said method comprising the steps of:

placing said proximal end of said drainage catheter in fluid communication with said proximal end of said first catheter and said proximal end of said second catheter;

placing a first one-way valve in fluid communication with said first catheter between said proximal end and said at least one opening such that said first one-way valve permits fluid flow from said at least one opening to said proximal end with a predetermined opening pressure greater than zero, and said first one-way valve effectively blocks fluid flow from said proximal end to said at least one opening;

placing a distal end of the first catheter in the brain spaced from the ventricles;

placing a second one-way valve in fluid communication with said second catheter between said proximal end and said at least one opening such that said second one-way valve permits fluid flow from said at least one opening to said proximal end with a predetermined opening pressure greater than zero, said second one-way valve effectively blocks fluid flow from said proximal end to said at least one opening; and placing a distal end of the second catheter in one of the ventricles of the brain.

\* \* \* \* \*